(12) United States Patent
Lu

(10) Patent No.: US 11,365,405 B2
(45) Date of Patent: Jun. 21, 2022

(54) METHOD OF REMOVING NUCLEIC ACIDS FROM HUMAN PLASMA

(71) Applicant: ANCHOR MOLECULAR INC., Pleasanton, CA (US)

(72) Inventor: Yabin Lu, Pleasanton, CA (US)

(73) Assignee: ANCHOR MOLECULAR INC., Pleasanton, CA (US)

( * ) Notice: Subject to any disclaimer, the term of this patent is extended or adjusted under 35 U.S.C. 154(b) by 78 days.

(21) Appl. No.: 16/824,665

(22) Filed: Mar. 19, 2020

(65) Prior Publication Data
US 2020/0299673 A1 Sep. 24, 2020

Related U.S. Application Data

(60) Provisional application No. 62/821,901, filed on Mar. 21, 2019, provisional application No. 62/821,424, filed on Mar. 20, 2019.

(51) Int. Cl.
*C12N 15/10* (2006.01)
*C12Q 1/6806* (2018.01)

(52) U.S. Cl.
CPC ........ *C12N 15/1006* (2013.01); *C12Q 1/6806* (2013.01)

(58) Field of Classification Search
CPC .............. B01D 15/363; B01D 15/3804; B01D 15/362; C12N 15/1006; C12N 15/1003; C12N 15/101; C12N 15/1017; C12Q 1/6806
See application file for complete search history.

(56) References Cited

U.S. PATENT DOCUMENTS

2011/0020924 A1 1/2011 Templeton
2018/0228831 A1 8/2018 Larson et al.

FOREIGN PATENT DOCUMENTS

JP H055731 A * 1/1993
WO 2016065295 A1 4/2016

OTHER PUBLICATIONS

Machine Translation of JPH055731A. (Year: 1993).*
International Search Report PCT/US2020/023734, dated Jun. 26, 2020.

* cited by examiner

*Primary Examiner* — Young J Kim
(74) *Attorney, Agent, or Firm* — Yong Chen; Lin Sun-Hoffman; Liu Chen & Hoffman LLP

(57) ABSTRACT

The invention is directed to methods and kits which utilize an immobilized solid support to extract the nucleic acids present in the human plasma sample Immobilized solid support further comprises: a) a pre-treated solid support material b) M-Aminophenylboronic acid (APBA), and c) levoglucosenone. The components and methods for activating solid support and extraction of nucleic acids used in the invention provide for high extraction efficiency and the resultant product is a highly purified plasma which is almost completely free of nucleic acids.

12 Claims, 4 Drawing Sheets

METHOD OF REMOVING NUCLEIC ACIDS FROM HUMAN PLASMA

CROSS REFERENCE TO RELATED APPLICATIONS

This application claims priority to U.S. Provisional Application No. 62/821,424, filed Mar. 20, 2019, and U.S. Provisional Application No. 62/821,901, filed Mar. 21, 2019, the disclosures of both of which are incorporated herein by reference in their entireties.

TECHNICAL FIELD

The invention relates to a method for the removal of nucleic acids from human plasma and a kit based on the method thereof. The invention in particular relates to a method of removing plasma DNA from the plasma sample to obtain a DNA-depleted plasma or serum that can be used in a variety of applications (such as a standard matrix in various clinical diagnostic tests).

BACKGROUND

With recent advances in DNA-based technology such as Next Generation Sequencing (NGS) and digital PCR (dPCR), diagnostic tests based on plasma cell free-DNA (cfDNA) have become increasingly important in liquid biopsy of genetic disease. Compared to current tissue-based biopsy procedures, liquid biopsy based on plasma cfDNA has several advantages. It is non-invasive, capable of monitoring test results in real time, repeatable, and capable of detecting a variety of mutations originated from heterogenous tumor tissues. The circulating tumor DNAs (ctDNA) are fragments of the DNA released by the tumor cells in the plasma. They are important biomarkers for cancer diagnosis, prognostication, treatment selection, and monitoring of the cancer burden.

As with any assay analyte that is plasma based, using plasma as a matrix is necessary for the quality controls for monitoring both the cfDNA extraction and downstream steps. This is important because the detection of trace amount of mutations in the plasma is such a sensitive task that any tiny amount of interference could result a particular mutation being misrepresented. Plasma DNA extraction is one of the most important and often an inconsistent step in sequencing or PCR-based DNA analysis. Numerous unknown carbohydrate, protein or lipid factors, either inhibitory or facilitory, can affect different steps of the extraction such as capturing, washing, or elution. Many DNA binding factors escaping the washing steps may be co-eluted with the DNA and may interfere with biochemical reactions in downstream DNA sequencing steps.

The effect of plasma factors on cfDNA extraction has not been extensively studied due to the lack of sufficient amount of patient plasma with well-defined in genetic content that can be used for making true-plasma based reference standards and controls. The majority of the cfDNA or ctDNA exist in the blood as small fragments as a result from protection from nuclease by one-(~170 bp), two-(~340 bp) and three-(~510 bp) nucleosomes. However, the compositions of the cfDNA such as its mutation profile from plasma of any given patient is usually unknown. This makes it hard to prepare a reference standard or control having a known certain genetic content. In addition, the amount of cfDNA can vary in a range from 1 to 30 ng per milliliter. The presence of variable amount of large DNA with fragment sizes greater than a few thousand base pairs may bias the measurement of the smaller-sized ctDNA.

Currently, there are only "synthetic plasma" based cfDNA controls available on the market. Synthetic plasma doesn't contain sufficient variety of molecules that exist in the true human plasma. In addition, adding extragenous proteins originated from plant, animal, bacteria or cell-lines (for recombinant proteins) also introduces unpredictable DNA contaminations from each respective source. Unknown molecules or factors in synthetic plasma can interfere with the analysis of ctDNA, inhibit or affect the sample processing treatment in different ways from what are in the true human plasma. Without these molecules from the true plasma, quality control samples made with "synthetic plasma" cannot fully mimic the real patient sample. For this reason true plasma-based calibrators and controls need to be used in all the diagnostic tests using plasma samples.

Thus, there is a need to obtain DNA-depleted true or real human plasma that can be widely used in plasma-based cfDNA/ctDNA tests in the future.

Existing methods of separating DNA from plasma generally utilize the affinity of DNA to silica. This type of method can remove 85 to 95% of DNA from plasma even after repeated application of the silica matrices. Low level of DNA as high as one nano gram per milliliter still remains in the plasma. The method of the present invention overcomes the drawbacks of the prior art. The treated plasma contains much less remaining DNA which can be as low as 0 to 100 pico gram per milliliter. The present invention offers improved method and kits thereof for the effective extraction of nucleic acids from plasma and thereby obtaining nucleic acid free plasma.

SUMMARY

The present invention provides a method for removal of nucleic acids from plasma, the method comprising the steps of: a) incubating an amount of human plasma with a immobilized solid support comprising: a pre-treated solid support material, M-Aminophenylboronic acid (APBA), and levoglucosenone, and b) extracting nucleic acids from the plasma to obtain a purified human plasma that is essentially free of nucleic acids. As used herein, human plasma "essentially free of nucleic acids" means that the purified human plasma contains less than 100 pg/ml of DNA or RNA. This is also referred to as nucleic acid depleted plasma.

The present invention also provides a method for activating the solid support material, the method comprises contacting a solid support material with cross-linking agents in pre-determined suitable conditions to obtain an activated solid support material; and then incubating the pre-treated solid support material with M-Aminophenylboronic acid (APBA) and levoglucosenone in pre-determined suitable conditions followed by the addition of a blocking agent to obtain the immobilized solid support.

The present invention also provides a kit for extraction of nucleic acids from plasma, the kit comprising: An immobilized solid support that further comprises: a pre-treated solid support material, M-Aminophenylboronic acid (APBA), and levoglucosenone. The plasma can be incubated with the immobilized solid support under pre-determined conditions for the extraction of nucleic acids from plasma to obtain nucleic acids and a nucleic acid free plasma.

The present invention also provides a method to obtain plasma essentially free of nucleic acids (or nucleic acid depleted plasma). The method can be used for:

Preparing DNA-depleted human plasma and derivatives of the plasma

Preparing DNA-depleted animal plasma and its derivatives

Preparing any similar biological fluid or medium to be DNA-depleted

The plasma can be further processed by defibrination. The processed plasma or similar biological fluid obtained by the method disclosed in the invention is a highly purified product which can be used as:

Negative control sample for diagnostic test of cfDNA.

Matrix used for making positive controls or reference standards or calibrators for clinical diagnostic tests, e.g., cfDNA test.

Matrix used for making positive or negative controls or reference standards or calibrators for liquid biopsy controls.

Matrix used for making quality controls for monitoring the quality of the sample preparation step such as DNA extraction DNA-free human or animal plasma or serum as a composition of cell-culture media

DETAILED DESCRIPTION

Figure 1:
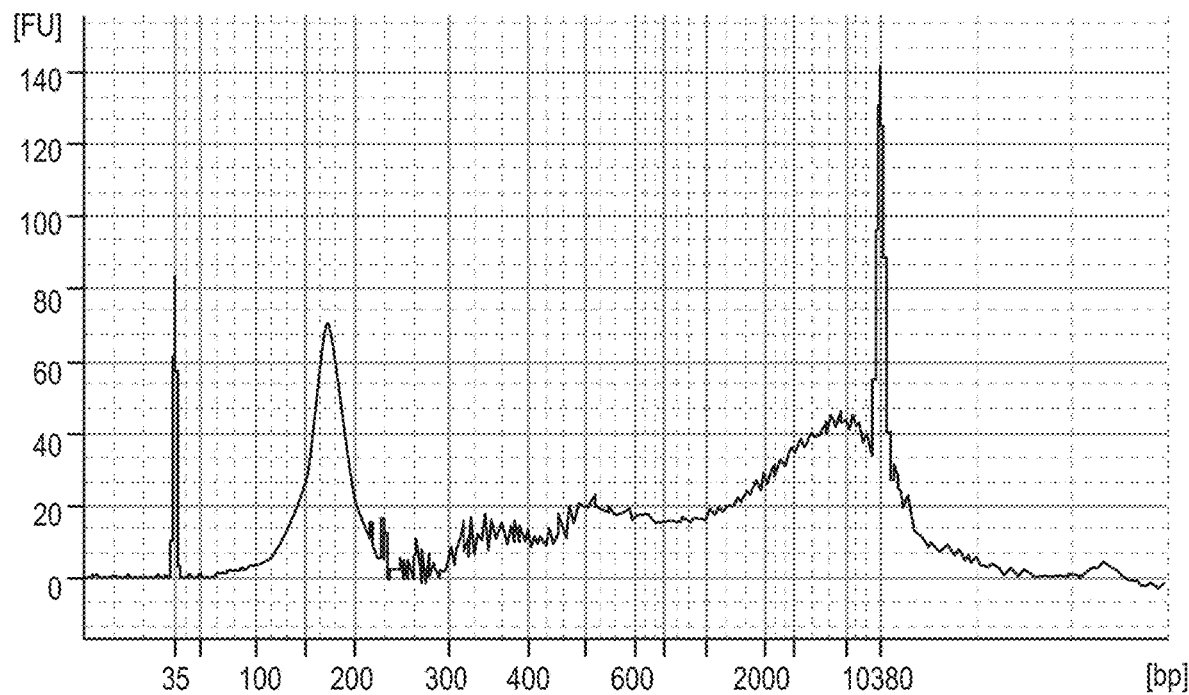
FIGS. 1 and 2 show DNA analysis results of certain samples.

In the following description, various aspects of the invention will be described. For the purposes of explanation, specific details are set forth in order to provide a thorough understanding of the invention. Alterations and further modifications of the inventive features, and additional applications of the principles of the invention as have been illustrated herein, which would occur to one, skilled in the relevant art and having possession of this disclosure, are to be considered within the scope of the invention.

The definitions and certain terms and acronyms which may be used in the description are provided as follows:

The term "cross-linkers" or "cross-linking agents" refers to chemical reagents used to conjugate molecules together by a covalent bound. Crosslinkers may react with carboxyls to form an intermediate that can stabilize upon reaction with amines, forming a peptide bond. In some embodiments, the crosslinkers can include a cardodiimide such as EDAC (1-ethyl-'I-[3-dinmmethvlaminopropyl carbodiimide), and a stabilizer such as N-hydroxy succinimide (NHS). The activation forming an N-hydroxysuccinimidyl ester (NHS-ester) by consecutively reacting carboxylic acids with a carbodiimide and NHS.

The term "MES buffer" refers to MES solution having a pKa value of about 6.15.

The term "blocking agent" refers to the compounds or the molecules used for quenching the excess cross-linking agents, or to deactivate the excess functional groups present on the support material.

The term "base solid support" refers to matrix material which provides carboxyl groups to be crosslinked to ligands bearing primary amine. The final functionalized solid support provides a large surface area for the contact between the nucleic acids and the ligand immobilized thereon, which is important for capturing nucleic acids from plasma samples.

The present invention relates to a method of removal of nucleic acids from the bodily fluids which can be further used for various diagnostic tests. The bodily fluids can be selected from, but not limited to, blood, plasma, serum, urine, saliva, ascites fluid, synovial fluid, amniotic fluid, semen, cerebrospinal fluid, follicular fluid and other fluid used in liquid biopsy tests. In one embodiment, the method according to the present invention provides a very high removal efficiency of the nucleic acids from the plasma. The resulting nucleic acid free plasma can be used for various applications, such as:

1. DNA-negative control sample for diagnostic test of cfDNA
2. Matrix for making positive controls or reference standards or calibrators for cfDNA test
3. Matrix for making positive or negative controls or reference standards or calibrators for liquid biopsy controls
4. Matrix for making quality controls for monitoring the quality of the sample preparation step such as in DNA extraction procedure.
5. DNA-free cell culture media or other biological media.

In another embodiment, the present invention provides a highly efficient method for the extraction of nucleic acids from the bodily fluids. By using the method according to the present invention almost all of the nucleic acids can be recovered from very small sample volumes. This is very advantageous specially in tests where the sample volumes are very small. This method finds its application in a number of tests such as non-invasive prenatal testing NIPT, ctDNA tests and the like.

In yet another embodiment, the present invention provides a kit for the purpose of extraction of the nucleic acids from a bodily fluid, wherein the bodily fluid can be selected from, but not limited to, blood, plasma, serum, urine, saliva, ascites fluid, synovial fluid, amniotic fluid, semen, cerebrospinal fluid, follicular fluid and other fluid used in liquid biopsy tests. The kit can comprise pre-treated solid support material, with M-Aminophenylboronic acid (APBA), and levoglucosenone.

In yet another embodiment, the kit may further comprise NaOH solution, deionized water, MES buffer, PBS buffer, cross-linking agents, a blocking agent and $CaCl_2$. The components of the kit are used to first activate the solid support material which is selected from the group of, but not limited to, plastic or latex beads, fabric sheets, polymer sheets, membranes, and magnetic particles coated with a polymer, followed by the immobilization of the solid support material with the M-Aminophenylboronic acid (APBA) and levoglucosenone to facilitate the binding of the nucleic acids to the solid support, thereby enabling the easy and efficient extraction of nucleic acids from the sample.

In yet another embodiment, the kit according to the present invention, is used for the removal of the nucleic acids, not limited to, cfDNA, ctDNA, cffDNA, cfRNA, ctRNA, DNA, RNA from body fluids. Kits provided in the invention can be used for preparing nucleic acid depleted plasma. The nucleic acid depleted plasma thus obtained is essentially free of nucleic acids.

In other embodiment, the present invention provides a method for obtaining a functionalized solid support. The method comprises contacting a base solid support material with a cross-linking agent in pre-determined suitable conditions; and then incubating the pre-treated solid support material with M-Aminophenylboronic acid (APBA) and levoglucosenone in pre-determined suitable conditions followed by the addition of a blocking agent to obtain the functionalized solid support.

The base solid support material can be selected the group consisting of, but not limited to, plastic or latex beads, nonwoven fabric sheets, woven fabric sheets, polymer sheets, membranes, magnetic particles coated with a polymer, paper, porous particulates, cellulose, wood, and glass fibers. In some embodiments, the base solid support material can be pre-carboxylated.

The cross-linking agents in the invention may be selected from carbodiimides. Any carbodiimide known to be used in this field as a carboxyl group activator, can be used for the purposes of the invention. Carbodiimides which can be used as activators within the framework of the invention are selected from the group of, but not limited to, EDAC (1-ethyl-3-(3-dimethylaminopropyl)carbodiimide), CMC (N-cyclohexyl-N'-(2-morpholinoethyl)carbodiimide methyl-p-toluenesulfonate), DCC (dicyclohexyl-carbodiimide). The cross-linking reagents can further include N-hydroxy succinimide (NHS).

M-Aminophenylboronic acid (APBA) and levoglucosenone are used as co-ligands which are immobilized over the solid support material.

Low molecular weight amine can be used for stabilizing the cross-linking reaction, or for quenching the functional groups present on the immobilized solid support as the blocking or quenching agents. The blocking or quenching agents can be selected from the group of, but not limited to, a mono, di, or multifunctional agent, preferably a primary amine Typical low molecular weight amines used to regulate or deactivate excess cross-linking agents are alanine, glycine, ethanolamine, threonine, alanine, lysine, serine, 2-aminoadipic acid and glutathione. Other compounds used as blocking agents are terminators such as bisulfites and diols capable of quenching aldehydes, alcohols with low molecular weight for quenching activated carboxylic acids, activated halides, isocyanates, and sulfhydryls for deactivating epoxide and vinyl groups present on the solid support material.

In yet another embodiment, the invention provides a method for the removal of nucleic acids from plasma, the method comprising the steps of: a) obtaining the supernatant either before or after defibrination of the plasma and incubating the obtained separated supernatant with the functionalized solid support and $MgCl_2$ under pre-determined conditions suitable to allow binding of the nucleic acids to the functionalized solid support; b) centrifuging the nucleic acids bound functionalized solid support to recover the supernatant and discard the pellet.

The following examples illustrate the aspects of the present invention:

Example 1

A functionalized support material is prepared according to the following procedure: a) Washing 1 ml the carboxylated latex beads (with diameter between 0.08 to 9.7 μm) with 0.01M NaOH solution for 10 minutes, followed by washing with deionized water. This is done to remove extra liquid present on the solid support material. b) Adding a mixture of 1 ml of EDAC agent (at a concentration range between 50 to 1000 mg/ml) and 1 ml of NHS (at a concentration range between 50 to 500 mg/ml) to the washed solid support material, and incubating the mixture for 1 to 120 min with slow vortexing at temperature range between 25 to 100□. The mixture of EDAC and the NHS is prepared in 25 mM MES at pH 5. c) Washing the solid support material obtained from step b) with MES buffer and adding a 1 ml mixture of M-Aminophenylboronic acid (APBA) at 0.05 to 0.2 g/ml and levoglucosenone (0.01 to 0.1 g/ml) in 1:1 water:dihydrolevoglucosenone mixture (pH 7.4) with vortexing overnight at 4° C.; d) Adding a ethanolamine in PBS buffer (at 50 mM, pH8.0) to the mixture obtained from step c) and incubate with vortexing for 60 min in room temperature, followed by washing the solid support material with PBS buffer to obtain the functionalized solid support.

Example 2

A method for removal of cell-free DNA from plasma is performed according to the following procedure: thawing of human plasma sample containing anti-coagulants, in a water bath for a period of time from 1 to 14 hours. a) mixing the plasma with 5% to 30% w/v $CaCl_2$, to form an admixture to a percentage of 0.5 to 10% (v:v of $CaCl_2$:plasma), incubating the mixture at 4° C. overnight to allow defibrination of fibrin in the plasma. b) centrifuging the incubated admixture to form pellet and supernatant. c) separating the supernatant from the pellet. d) incubating the separated supernatant with a functionalized solid support of the present invention and 1 to 5 mM $MgCl_2$ in 20 mM phosphate buffer overnight to allow binding of the cell-free nucleic DNA to the functionalized solid support. e) centrifuging the cell-free DNA bound functionalized solid support in step d) at 10,000×g for 15 minutes at 2-8° C. to recover the supernatant and discard the pellet. f) repeating step e) one to two times if necessary. g) subjecting the recovered supernatant to dialysis in Phosphate Buffered Saline (PBS) with Tangential flow filtration (TFF).

The plasma product obtained is brownish yellow in color with protein concentration of >5 g/dL. This can be used as negative control or calibration source on various diagnostics test, such as lipid biopsy, noninvasive prenatal testing (NIPT), cancer management etc.

Example 3

A method for isolating cell-free DNA from plasma is performed as follows: thawing of human plasma sample containing stabilizers, not limited to, EDTA, sodium citrate, and other anti-coagulants, in a water bath for a period of time from 1 to 14 hours. a) mixing the plasma with 5% to 30% w/v $CaCl_2$, to form an admixture to a percentage of 0.5 to 10% (v:v of $CaCl_2$:plasma), incubating the admixture at 4□ overnight to allow defibrination of fibrin in the plasma. b) centrifuging the incubated admixture to form pellet and supernatant. c) separating the supernatant from the pellet. d) incubating the separated supernatant with functionalized magnetic solid support and $MgCl_2$ (1 to 5 mM in 20 mM phosphate buffer) overnight to allow binding of the cell-free nucleic DNA to the functionalized solid support. e) magnetically separating the cell-free DNA bound functionalized solid support in step d) to recover the beads and discard the supernatant. f), adding 100 mM NaCl, 1 mM EDTA (pH8.0), 10 mM Tris.Cl (pH 8.0), 50-70% Ethanol to the beads, vortexing the mixture followed by magnetic separation. g) repeat step f) one or more times to obtain almost all of the cfDNA present in the sample.

Example 4. DNA Testing

Sample 41: 20 ml of untreated plasma from a normal subject (human) Sample 42: 20 ml of plasma treated as per the methods disclosed in Example 2.

Subjecting both samples to DNA extraction with standard cfDNA extraction kits which are available from the market. The extracted DNA from both the sample 41 and sample 42 were analyzed with Bioanalyzer 2100 or quantitated with the DeNovix Ultra High Sensitive Kit.

Figure 2:
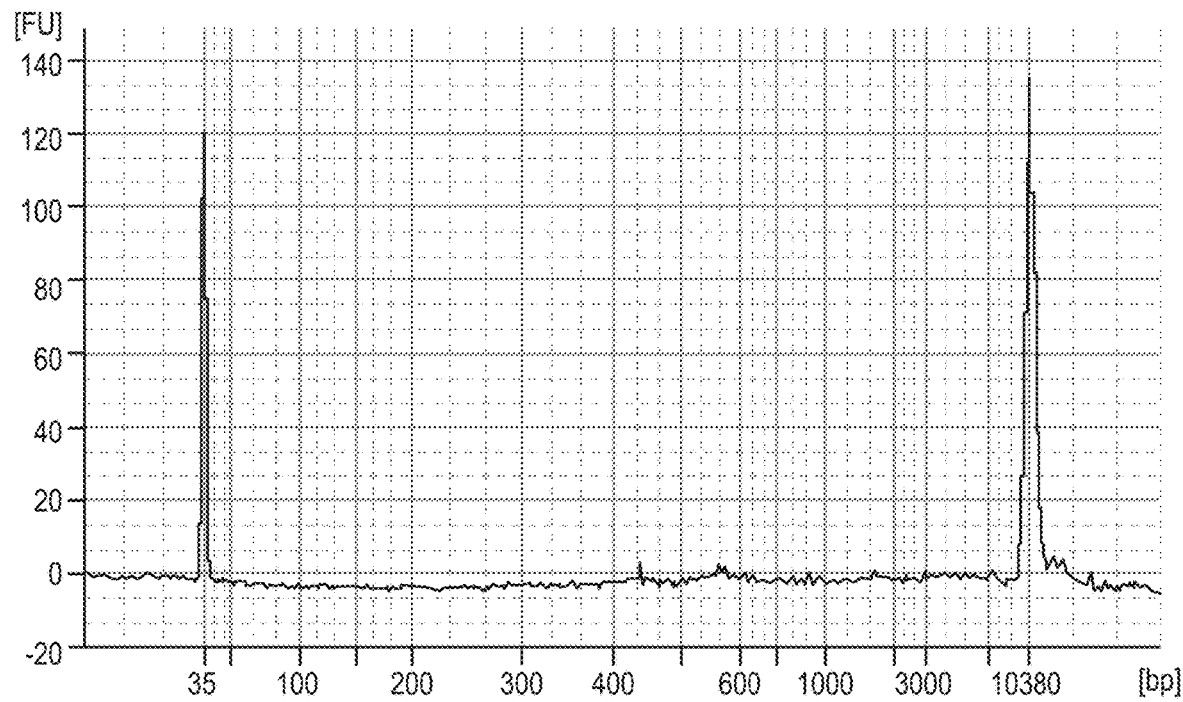

Analysis results shown in FIGS. 1 and 2 respectively indicate that DNA from the sample 41 was quantitated to be 7 ng/ml, and DNA from sample 42 was quantitated to be less than 0.02 ng/ml. (Note the bumps in the middle are DNA signals detected along the x-axis (size of DNA). The two sharp peaks at the left most and the right most are DNA size markers, not DNA from the sample).

Example 5. Utility of DNA Depleted Plasma as Matrix for ctDNA Reference Standards Sample 51: Purified mixture of mutated ctDNA and wildtype cfDNA fragments were added to the DNA-depleted plasma sample, obtained from the method disclosed in the invention. The mutated ctDNA is comprised of BRAF V600E mutation.

Sample 52: Untreated plasma sample taken from a normal subject (human).

Figure 3:
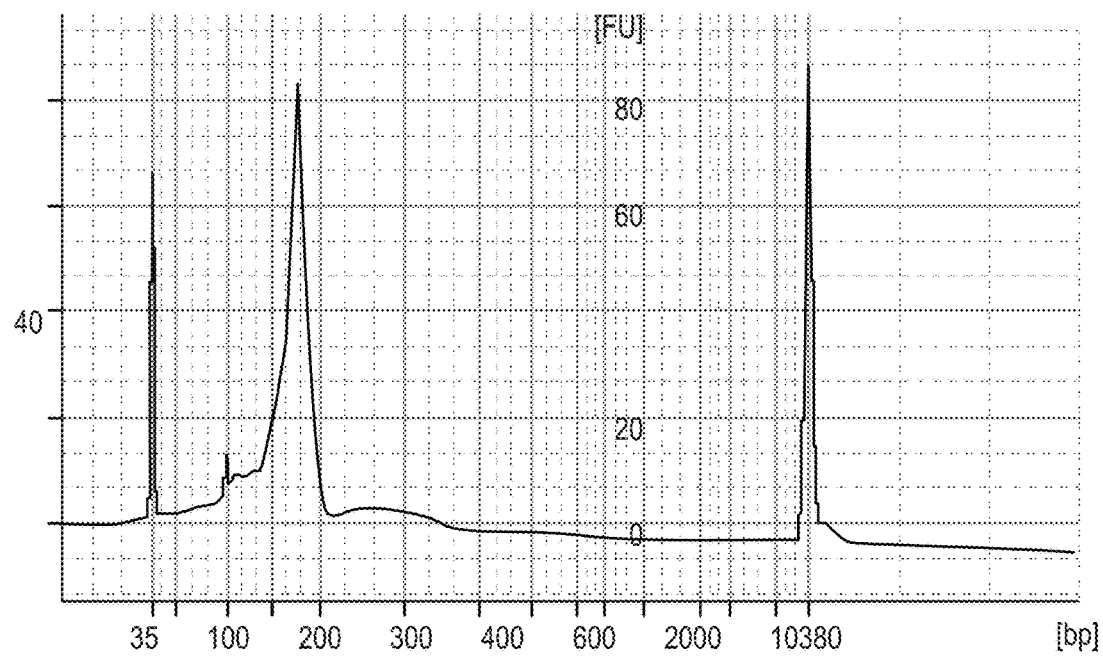
FIG. 3 shows DNA analysis results of certain plasma samples.

The plasma sample 51 and sample 52 were analyzed by a Bioanalyzer 2100 (loaded at 14 ng/ul). Results as shown in FIG. 3 (for sample 51) indicate that the purified mixture of mutated ctDNA and wildtype cfDNA fragments spiked into the DNA-depleted plasma (sample 51) mimics the cfDNA seen from normal plasma (sample 52).

Figure 4:
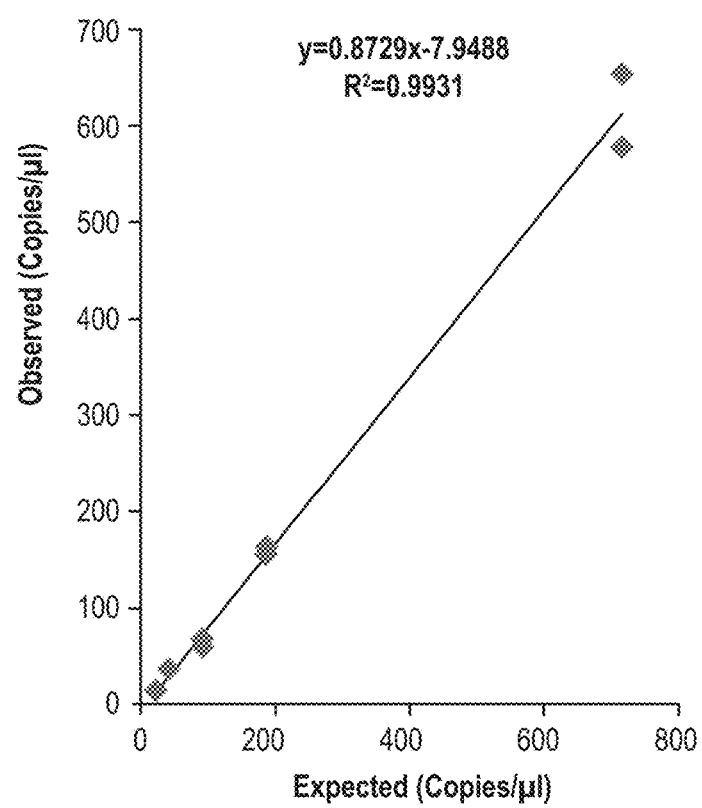
FIG. 4 is a plot showing expected DNA concentrations in a plasma sample against measured actual DNA concentrations from the plasma sample.

As shown in FIG. 4, the Spiked-in DNA fragments in sample 51, were extracted from the DNA-depleted plasma and from the extracted DNA the same BRAF V600E mutation was recovered as expected. The data points were obtained by plotting each of the points the expected (calculated by the amount that is put into the DNA-depleted plasma) DNA concentrations in the sample against the measured actual DNA concentration from the extracted plasma sample.

Figure 5:
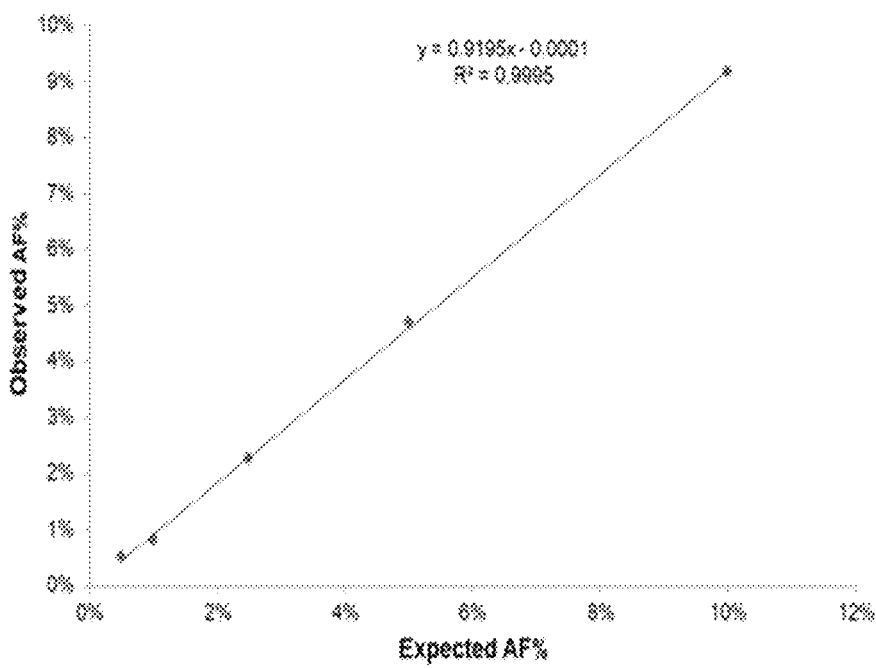
FIG. 5 is a plot showing the expected allele frequency of DNA in a sample against the measured actual allele frequency from the sample.

As shown in FIG. 5, the Allele Frequency (approximated by the percentage of the BRAF V600E mutation over the wildtype gene) of the recovered DNA's from the DNA-depleted plasma of the invention was as expected. The data points were obtained by plotting each of the points the expected (calculated by the amount that is put into the DNA-depleted plasma) Allele Frequency in the sample against the measured actual allele frequency from the extracted plasma sample.

Example 6

Sample 61: BRAF V600E fragments (200 copies/ul)
Sample 62: BRAF V600E fragments (800 copies/ul)

Figure 6:
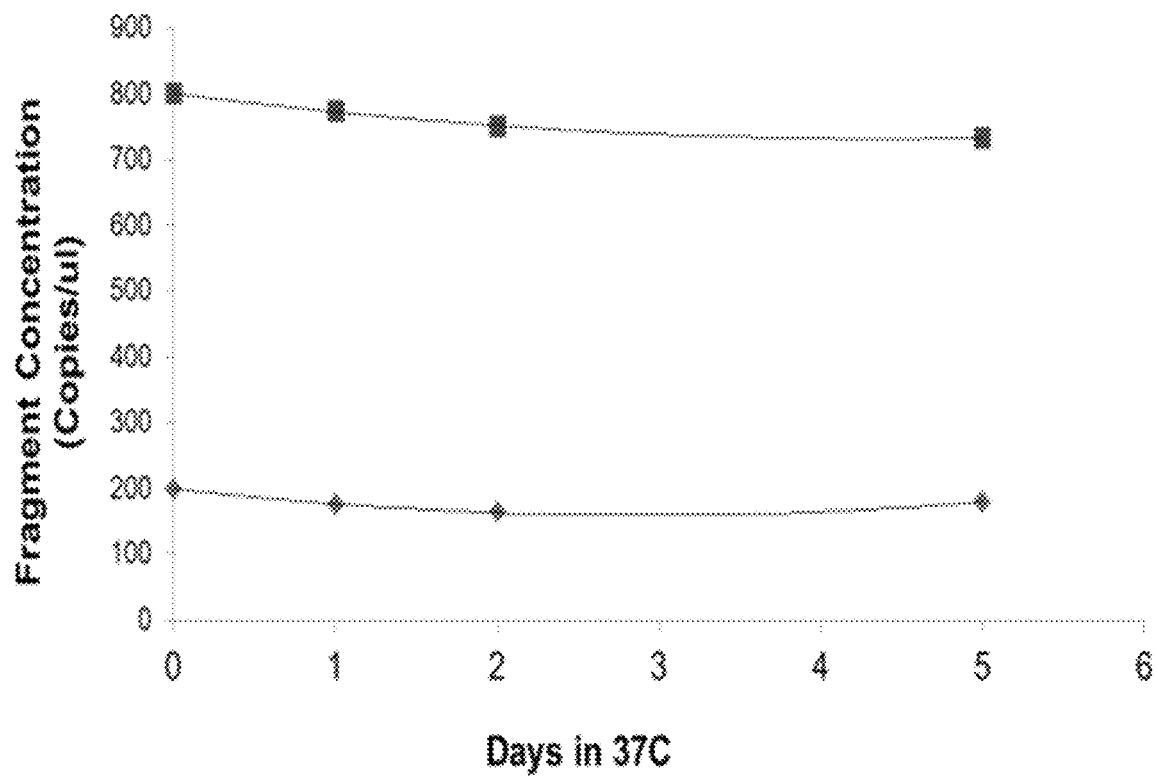
FIG. 6 shows concentrations of DNA fragments recovered from two samples over time.

These two samples of BRAF V600E fragments were added in DNA-depleted plasma and incubated at 37° C. for 5 days. DNA fragments were recovered at 90% and 92%, respectively, from the DNA-depleted plasma with the method disclosed in the invention, as shown in FIG. 6.

Figure 7:
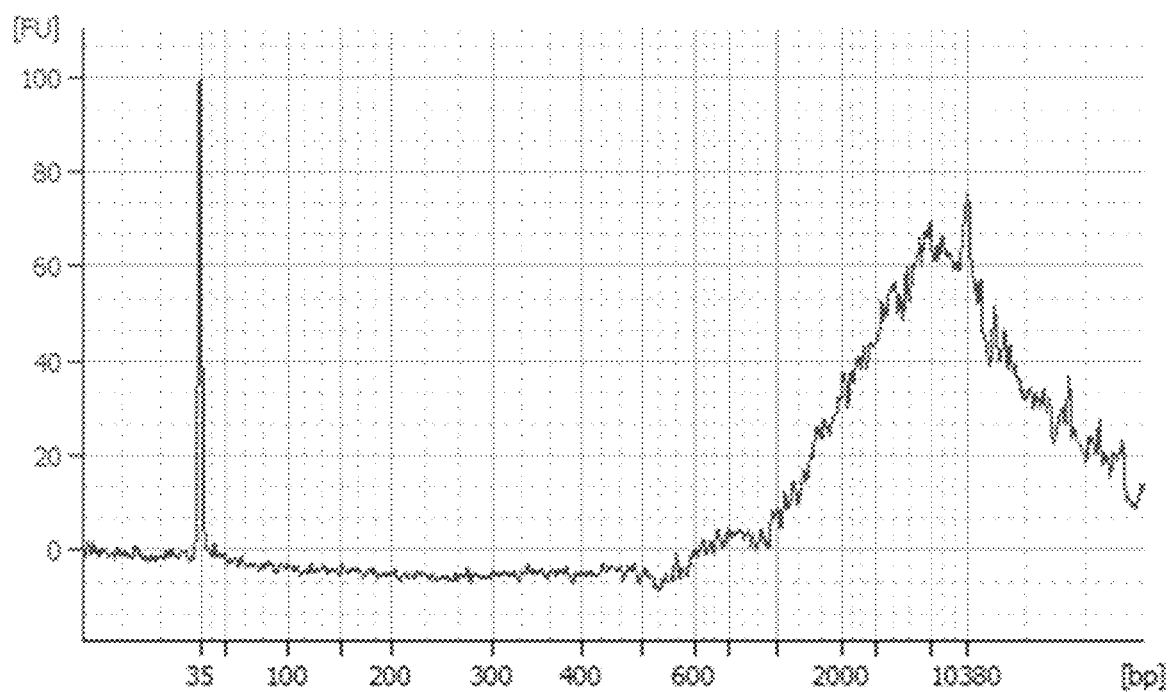
FIG. 7 shows genomic DNA which was purified from human cells was spiked into the DNA-depleted plasma.

Example 7. Utility of DNA-Depleted Plasma as Matrix for ctDNA Extraction Control Cells or genomic DNA can be quantitatively spiked into the plasma. The DNA-depleted plasma sample can serve as a monitoring control for genomic DNA removal during extraction for cfDNA preparation for ctDNA assays. FIG. 7 shows genomic DNA which was purified from human cells was spiked into the DNA-depleted plasma.

The purpose of the above description and examples is to illustrate some embodiments of the present invention without implying any limitation. It will be apparent to those of skill in the art that various modifications and variations may be made to the components of the kit and method of the present invention without departing from the spirit or scope of the invention. All such modifications will be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention.

The invention claimed is:

1. A method for removal of nucleic acids from plasma, the method comprising the steps of:
   incubating a plasma with a functionalized solid support comprising a solid support material pre-treated with 1) M-Aminophenylboronic acid (APBA) and 2) levoglucosenone; and
   extracting nucleic acids from the plasma to obtain a plasma that is essentially free of nucleic acids.

2. The method of claim 1, wherein the functionalized solid support was obtained by:
   (a) pre-treating a base solid support material with cross-linking agents to generate a treated base solid support material;
   (b) incubating the treated base solid support material generated in (a) with 1) M-Aminophenylboronic acid (APBA) and 2) levoglucosenone to generate an incubated solid support; and
   (c) adding a blocking agent to the incubated solid support.

3. The method of claim 1, wherein the nucleic acids are selected from DNA or RNA.

4. The method of claim 1, wherein the solid support material is selected the group consisting of plastic or latex beads, fabric sheets, polymer sheets, membranes, and magnetic particles coated with a polymer.

5. The method of claim 2, wherein the cross-linking agents include a carbodiimide.

6. The method of claim 5, wherein the carbodiimide is EDAC, CMC, or DCC.

7. The method of claim 2, wherein the crosslinking agents further include NHS (N-Hydroxysuccinimide).

8. The method of claim 2, wherein the blocking agent is selected from the group of ethanolamine, alanine, glycine, threonine, alanine, lysine, serine, 2-aminoadipic acid and glutathione.

9. The method of claim 2, wherein the base solid support is pre-carboxylated.

10. A method for removing nucleic acids from a human plasma sample, the method comprising the steps of:
    incubating a human plasma sample comprising an initial amount of nucleic acids with a functionalized solid support and $MgCl_2$, under predetermined conditions suitable to allow binding of the nucleic acids in the human plasma sample to the functionalized solid support, thereby obtaining an incubated mixture;

centrifuging the incubated mixture to obtain a supernatant and solid pellet, the solid pellet comprising aggregated functionalized solid support; and separating the supernatant and the solid pellet, thereby recovering the supernatant comprising plasma having an amount of nucleic acids less than the initial amount of nucleic acids; wherein the functionalized solid support comprises a solid support material pre-treated with M-Aminophenylboronic acid (APBA) and levoglucosenone.

11. A kit for extraction of nucleic acids from plasma, the kit comprising:
a functionalized solid support comprising:
a base solid support material pretreated with cross-linking agents; and
M-Aminophenylboronic acid (APBA) and levoglucosenone immobilized thereon.

12. The kit of claim 11, wherein the base solid support material is selected the group consisting of plastic or latex beads, fabric sheets, polymer sheets, membranes, and magnetic particles coated with a polymer.

\* \* \* \* \*